US00PP36650P2

(12) United States Plant Patent
Koot

(10) Patent No.: US PP36,650 P2
(45) Date of Patent: May 6, 2025

(54) ***BUDDLEJA* PLANT NAMED 'Botex 013'**

(50) Latin Name: *Buddleja davidii*
Varietal Denomination: Botex 013

(71) Applicant: Johannes Adrianus Maria Koot, Kaatsheuvel (NL)

(72) Inventor: Johannes Adrianus Maria Koot, Kaatsheuvel (NL)

(73) Assignee: BOTANIC EXPERIENCE B.V., Kaatsheuvel (NL)

( * ) Notice: Subject to any disclaimer, the term of this patent is extended or adjusted under 35 U.S.C. 154(b) by 0 days.

(21) Appl. No.: 18/912,731

(22) Filed: Oct. 11, 2024

(51) Int. Cl.
*A01H 6/00* (2018.01)
*A01H 5/02* (2018.01)

(52) U.S. Cl.
USPC ..... Plt./242

(58) Field of Classification Search
USPC ..... Plt./242
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Buddleja* plant named 'Botex 013' that is characterized by its very compact, dense, and neat and naturally overall rounded plant shape plant habit, its flowers that are white with orange centers in color, its suitability for growing in small containers, and its quick flowering with a very floriferous blooming habit.

3 Drawing Sheets

Botanical classification: *Buddleja davidii.*
Variety denomination: 'Botex 013'.

CROSS-REFERENCE TO RELATED APPLICATIONS

This application is related to a European Community Plant Variety Office (CPVO) Plant Breeder's Rights Application No. 2023/1788 filed on Sep. 13, 2023, under 35 U.S.C. 119(f), the entire contents of which is incorporated by reference herein. The Applicant received the information for the Plant breeders' rights application directly from the Inventor. This application is also co-pending with U.S. Plant Patent Applications filed for plants derived from the same breeding program that are entitled *Buddleja* Plant Named 'Botex 003' (U.S. Plant Pat. No. 34,525) and *Buddleja* Plant Named 'Botex 008' (U.S. Plant patent application Ser. No. 18/824,902), *Buddleja* Plant Named 'Botex 009' (U.S. Plant patent application Ser. No. 18/884,264), *Buddleja* Plant Named 'Botex 010' (U.S. Plant patent application Ser. No. 18/912,712), *Buddleja* Plant Named 'Botex 011' (U.S. Plant patent application Ser. No. 18/912,725), and *Buddleja* Plant Named 'Botex 012' U.S. Plant patent application Ser. No. 18/912,730).

BACKGROUND OF THE INVENTION

The present invention relates to a new and distinct cultivar of *Buddleja davidii* will be referred to hereafter by its cultivar name, 'Botex 013'. 'Botex 013' is a new shrub grown for use as an ornamental landscape plant and as a container plant.

The new cultivar of *Buddleja* is a selection from an ongoing breeding program conducted by the Inventor in Kaatsheuvel, The Netherlands with the goal of creating new cultivars of *Buddleja* with very neat and compact plant habits with suitability for growing in small containers combined with unique vibrant flower colors and floriferous blooming habits.

The Inventor made a cross in July of 2019 between unnamed and unpatented proprietary plants in the Inventor's breeding program; reference no. 18-025-02 as the female parent and reference no. 19011 as the male parent. The Inventor selected 'Botex 013' in August of 2022 as a single unique plant amongst the seedlings that resulted from the above cross.

Asexual propagation of the new cultivar was first accomplished by the Inventor using stem cuttings in Kaatsheuvel, The Netherlands in 2022. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Botex 013' as a unique cultivar of *Buddleja.*

1. 'Botex 013' exhibits a very compact, dense, and neat and naturally overall rounded plant shape plant habit.
2. 'Botex 013' exhibits flowers that are white with orange centers in color.
3. 'Botex 013' exhibits suitability for growing in small containers.
4. 'Botex 013' exhibits quick flowering with a very floriferous blooming habit.

The female parent of 'Botex 013' differs from 'Botex 013' in having longer inflorescences and a slightly taller plant height. The male parent of 'Botex 013' differs from 'Botex 013' in having a broader plant habit and a slightly taller plant height. 'Botex 013' can be compared to the *Buddleja* cultivars 'White Ball' (not patented) and 'Botex 003'. 'White Ball' differs from 'Botex 013' in having a slightly taller plant height, a slightly less compact plant habit, greenish grey leaves, and inflorescences that are less compact and slightly longer. 'Botex 003' differs from 'Botex 013' in having a less dwarf plant habit.

'Botex 013' can also be compared to the co-pending cultivars of *Buddleja*, 'Botex 008', 'Botex 009', 'Botex 010', 'Botex 011', and 'Botex 012'. 'Botex 008' differs from 'Botex 013' in having flowers that are magenta purple in color and in being taller in height. 'Botex 009' differs from 'Botex 013' in having flowers that are fuchsia pink in color. 'Botex 010' differs from 'Botex 013' in having flowers that are dark, vibrant purple in color. 'Botex 011' differs from 'Botex 013' in having flowers that are light pink in color. 'Botex 012' differs from 'Botex 013' in having flowers that are light violet blue in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by 27East, Dummen Orange, Cool Plants, Floral Daily, Bill Moore & Co., Ball Seed, National Garden Bureau, Visions Pictures, Plantenkwekerij Vechtdal, Dobrepole, Sweet Garden, University of Georgia Trial Gardens, Garden Center Magazine, Baldur-Netherland, and Zahradnictvi-spomysl.

BRIEF DESCRIPTION OF THE DRAWINGS

The accompanying color photographs illustrate the overall appearance and distinct characteristics of the new *Buddleja*. The photographs were taken of a one-year-old plant as grown in a greenhouse in a 19-cm container in Kaatsheuvel, The Netherlands.

The photograph in FIG. 1 provides a side view of the overall plant habit of 'Botex 013' in bloom.

Figure 1:
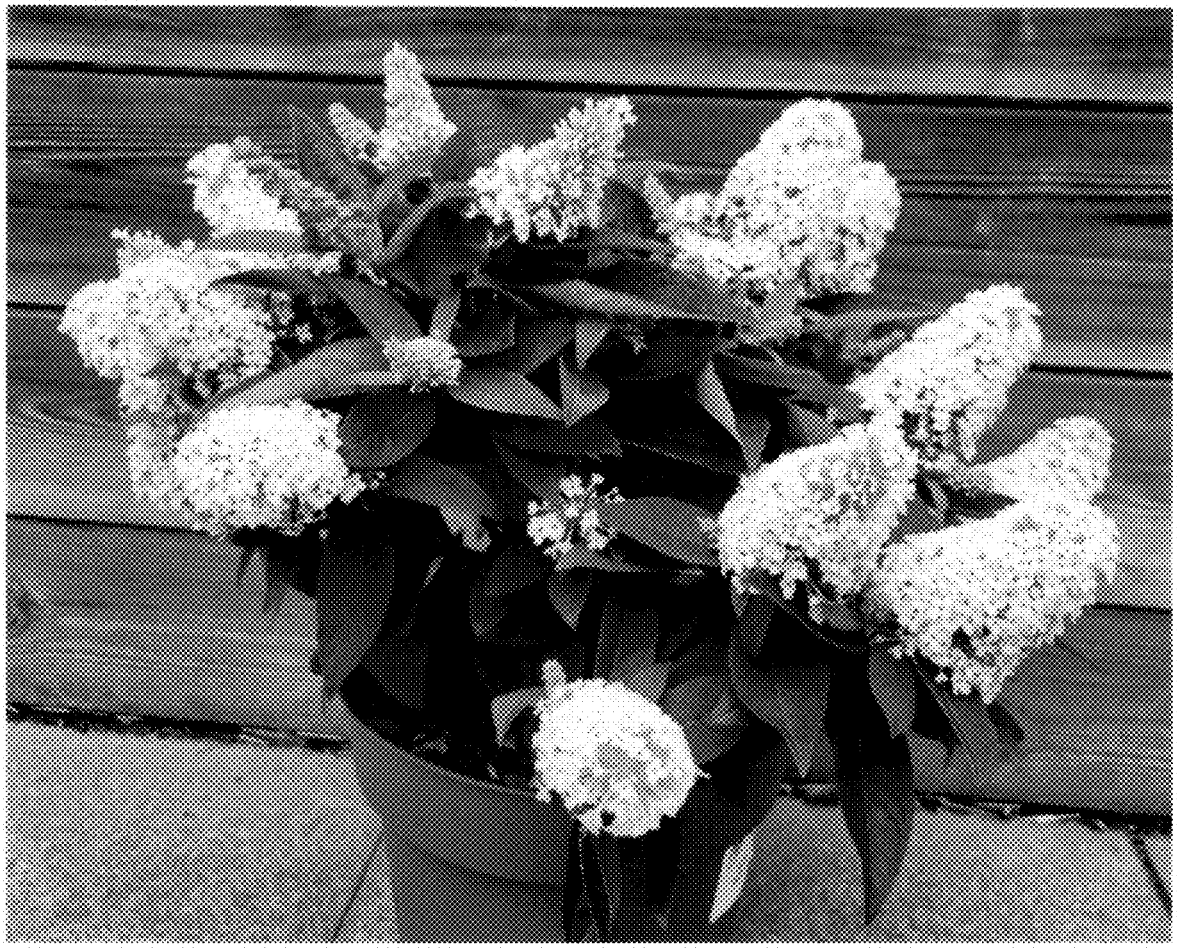
Figure 2:
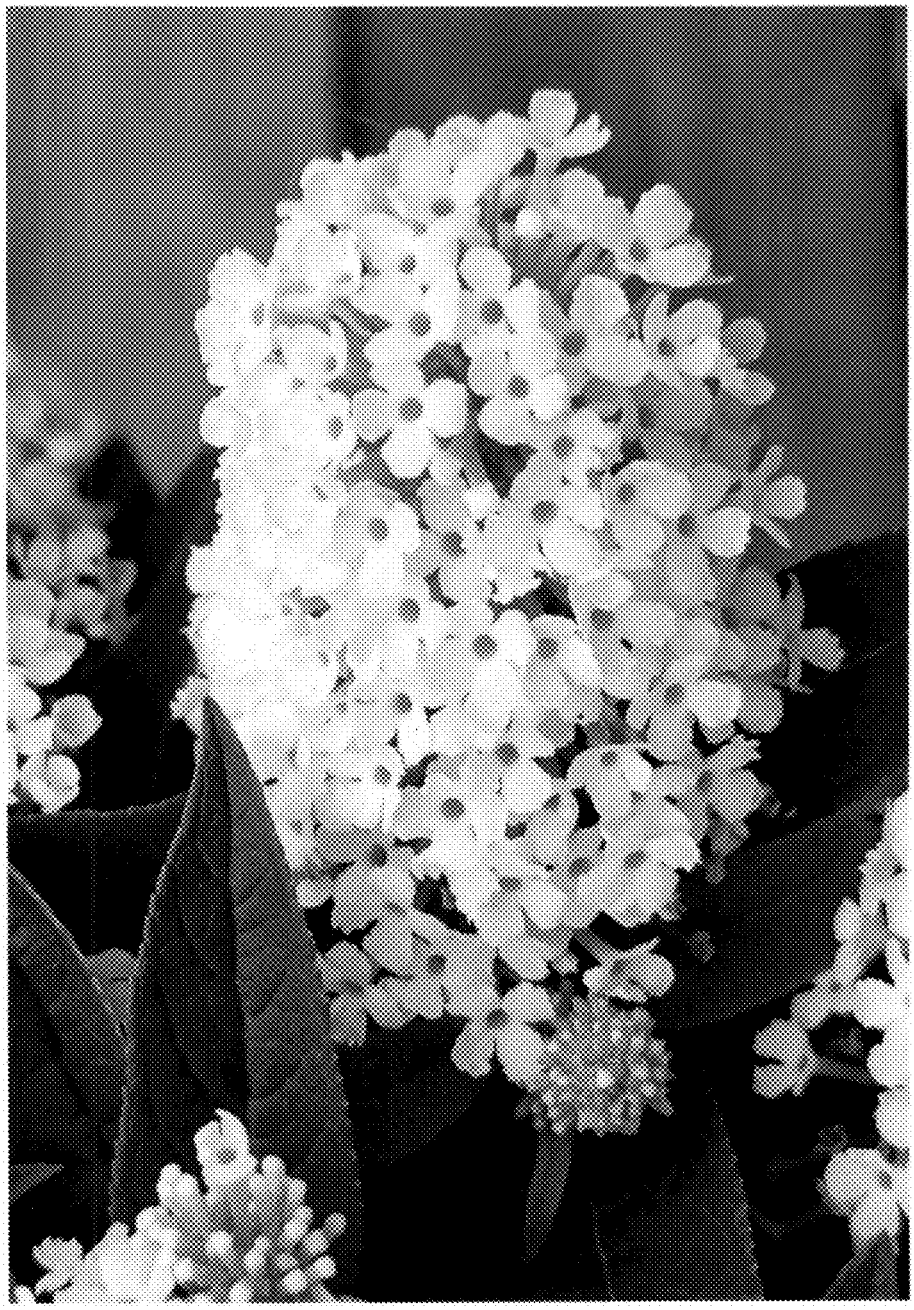

The photograph in FIG. 2 provides a close-up view of an inflorescence of 'Botex 013'.

Figure 3:
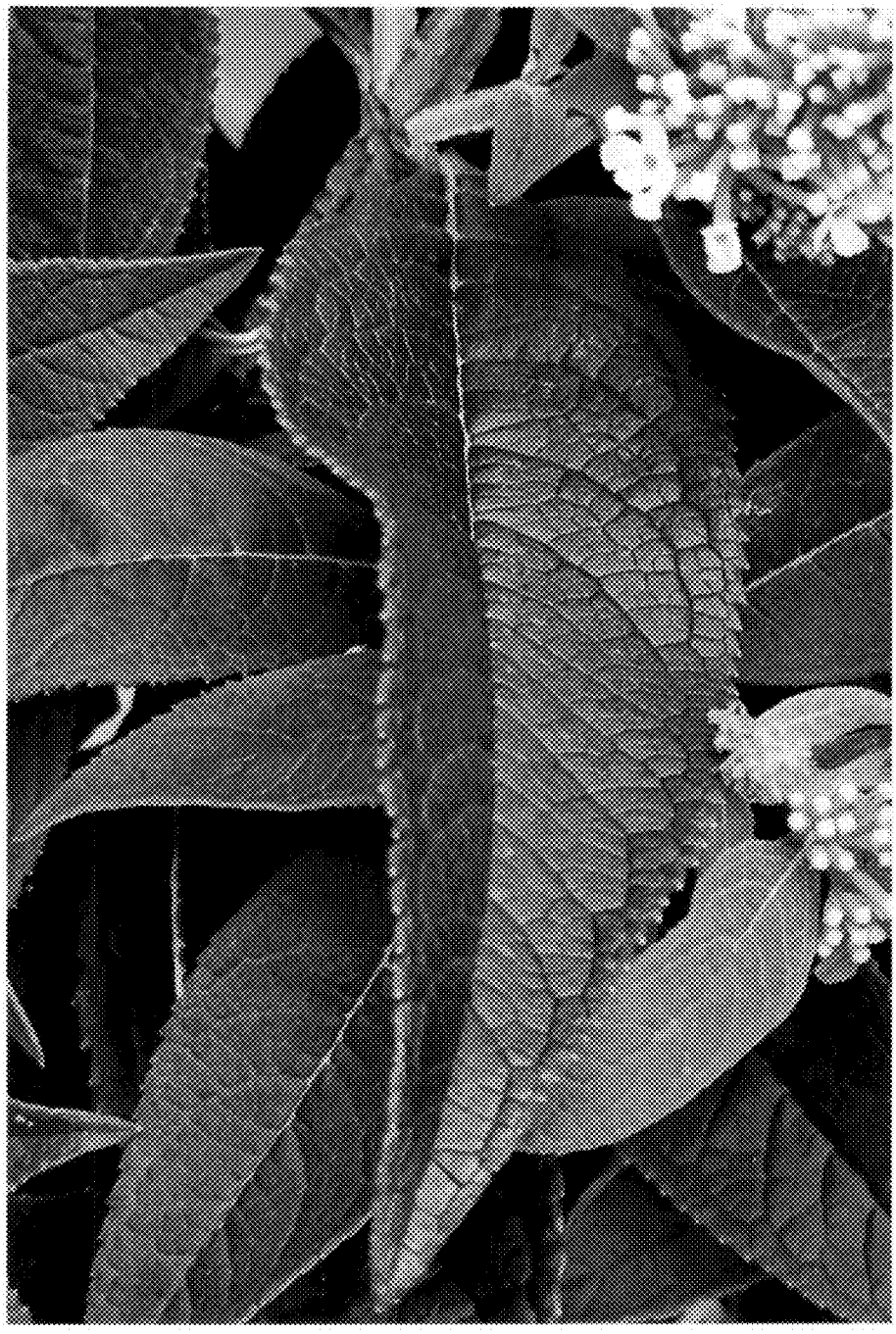

The photograph in FIG. 3 provides a close-up view of a leaf of 'Botex 013'

The colors in the photographs are as close as possible with the photographic and printing technology utilized and the color values cited in the Detailed Botanical Description accurately describe the colors of the new *Buddleja*.

DETAILED BOTANICAL DESCRIPTION

The following is a detailed description of one-year-old plants as grown in a greenhouse in 19-cm containers in Kaatsheuvel, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—July to October in The Netherlands.

*Plant type*.—Deciduous perennial shrub.

*Plant habit*.—Very compact, upright and naturally rounded, dense.

*Plant size*.—An average of 26 cm in height and 35 cm in width as a one-year-old plant grown in a container and reaches 50 cm in height and in spread as grown in the landscape.

*Cold hardiness*.—At least in U.S.D.A. Zone 5.

*Diseases and pests*.—No susceptibility and resistance to diseases or pests has been observed.

*Propagation*.—Stem cuttings.

*Root description*.—Fibrous.

*Root development*.—4 to 5 weeks to initiate roots and 6 to 7 weeks to fully root as a young plant in a P9 container.

*Growth rate*.—Vigorous, quick finishing.

Branch description:

*Branch shape*.—Quadrangular.

*Branch color*.—Young stems; 145B, mature and older woody stems; 199A.

*Branch strength*.—Strong.

*Branch size*.—Up to 17 cm in length and 4 mm in diameter.

*Branch surface*.—Pubescent.

*Branch aspect*.—Lateral stems held upright to an average angle of 30° to vertical.

*Branch internode length*.—Average of 2 cm.

*Branching*.—1 main branch, 7 secondary branches.

Foliage description:

*Leaf shape*.—Narrowly elliptical to elliptical.

*Leaf division*.—Simple.

*Leaf base*.—Attenuate.

*Leaf apex*.—Acute.

*Leaf fragrance*.—None.

*Leaf venation*.—Pinnate, upper surface; matches leaf color, lower surface; 191D, mid-vein 145B.

*Leaf margins*.—Serrate.

*Leaf arrangement*.—Opposite.

*Leaf attachment*.—Petiolate.

*Leaf surface*.—Both surfaces are smooth, matte, and pubescent.

*Leaf size*.—Up to 10.1 cm in length and an average of 3.4 cm in width.

*Leaf quantity*.—An average of 12 per main stem.

*Leaf color*.—Young upper surface; 137B to 137C, young lower surface; 191A, mature upper surface; NN137B, mature lower surface; 191C to 191D.

*Petioles*.—An average of 4 mm in length and 2 mm in diameter, strong, surface slightly pubescent, color; 145B.

Inflorescence description:

*Inflorescence type*.—Compound terminal and axial panicles, held upright.

*Inflorescence size*.—Up to 7 cm in height, up to 5.2 cm in width.

*Flower fragrance*.—Sweet, pleasant and medium strength.

*Lastingness of flowers*.—An average of 5 days, persistent.

*Flower buds*.—Oblong in shape, average of 5 mm in length and 1 mm in diameter, color; 145D and N88C.

*Flower aspect*.—Upright, slightly outward.

*Flower quantity*.—Average of 200 flowers per inflorescence and 22 inflorescences.

*Flower type*.—Single, salverform.

*Flower surface*.—All surfaces glabrous and matte.

*Flower size*.—An average of 9 mm in height, 5 mm in diameter, flower throat; 4 mm in length, 1 mm in diameter, flower tube; 5 mm in length, 1 mm in diameter.

*Peduncles*.—Primary; an average of 7 mm in length and 3 mm in diameter, secondary; an average of 3 mm in length and 1 mm in diameter, 145A in color, strong, glossy and pubescent surface.

*Pedicels*.—An average of 2 mm in length and 1.5 mm in diameter, 145B and 187A in color, strong, surface is pubescent.

*Calyx*.—Campanulate in shape, an average of 2 mm in length and 1.5 mm in diameter.

*Sepals*.—4, 1 whorl, rotate arrangement, fused into a campanulate shape, 2 mm in length, <1 mm in width, lanceolate in shape, acute apex, fused base, entire margin, both surfaces are matte and slightly pubescent, color; when opening and fully open upper and lower surface 145C.

*Petals*.—Average of 4, rotate, fused into salverform, 1 whorl, roughly spathulate in shape, slightly undulate margin, rounded apex, an average of 3 mm in length and 3 mm in width, color: petals; young and mature upper and lower surface NN155B, throat and tube; 22B.

Reproductive organs:

*Gynoecium*.—4 pistils, 3 mm in length, style; an average of 2 mm in length, 145B to 145C in color, stigma; elongated, 1 mm in length and 145B to 145C in color, ovary is 145B to 145C in color.

*Androecium*.—Stamens; 4, filament; 5 mm in length, 25B in color, anther; ovate in shape, 1 mm in length, 11D in color, pollen; low in quantity, too little to measure color.

*Fruit and seed*.—No seeds or fruit observed to date.

It is claimed:

1. A new and distinct cultivar of *Buddleja* plant named 'Botex 013' as herein illustrated and described.

* * * * *